United States Patent [19]

Lolivier et al.

[11] 4,062,901
[45] Dec. 13, 1977

[54] PROCESS FOR THE STABILIZATION OF METHYLENE CHLORIDE

[75] Inventors: Jacques Lolivier; André Ryckaert, both of Brussels, Belgium

[73] Assignee: Solvay & Cie., Brussels, Belgium

[21] Appl. No.: 346,269

[22] Filed: Mar. 30, 1973

[30] Foreign Application Priority Data

Apr. 7, 1972 Belgium .................................. 116047
Nov. 16, 1972 Belgium .................................. 124196

[51] Int. Cl.$^2$ .............................................. C07C 17/40
[52] U.S. Cl. .............................. 260/652.5 R; 252/305; 252/396
[58] Field of Search ...................................... 260/652.5

[56] References Cited

U.S. PATENT DOCUMENTS

| 2,492,048 | 12/1949 | Klabunde | 260/652.5 |
| 2,981,759 | 4/1961 | Cole et al. | 260/652.5 |
| 3,260,760 | 7/1966 | Domen et al. | 260/652.5 R |
| 3,326,989 | 6/1967 | Cormany et al. | 260/652.5 R |
| 3,406,213 | 10/1968 | Patron | 260/652.5 R |
| 3,423,476 | 1/1969 | Patron | 260/652.5 R |
| 3,546,304 | 12/1970 | Patron | 260/652.5 R |

OTHER PUBLICATIONS

Okamura et al., Chem. Abst. 72 (1970) 44723d.

*Primary Examiner*—Howard T. Mars
*Attorney, Agent, or Firm*—Spencer & Kaye

[57] ABSTRACT

Stabilized methylene chloride and process for stabilizing methylene chloride against its decomposition by supplying thereto 2-methylfuran and one or more expoxides.

9 Claims, No Drawings

PROCESS FOR THE STABILIZATION OF METHYLENE CHLORIDE

The present invention relates to a process for the stabilization of methylene chloride or of mixtures containing the same. It also covers methylene chloride which has been stabilized by this process.

Methylene chloride is frequently used in compositions for aerosols, as a solvent for the active materials and as depressor for the propellant (dichlorodifluoromethane, butane, propane, carbon dioxide, nitrogen hemioxide, etc.). However, methylene chloride tends to decompose on contact with metal surfaces or through the action of humidity, temperature, and so on. The resulting corrosion of metal surfaces becomes particularly great when the aerosol compositions contain water and/or an alcohol in addition to methylene chloride. This corrosiveness of methylene chloride is particularly great in respect of the metals frequently used in the manufacture of aerosol cans, such as aluminium or tinned steel.

It has already been proposed to alleviate the deterioration of metal surfaces caused by halogenomethanes by adding to them small amounts of a stabilizer of an organic nature. Among the stabilizers which have been proposed for the stabilization of halogenomethanes mention may be made, for example, of the nitroalkanes (Belgian Pat. No. 554,718 filed 4.2.1957 by FARBWERKE HOECHST A.G.). Nevertheless, these compounds are not sufficiently effective to stabilize methylene chloride when the latter is used mixed with water and/or an alcohol.

The present invention relates to a process permitting the stabilization of methylene chloride even in the presence of water and/or alcohol. It is concerned with a new process of stabilization of methylene chloride characterized in that 2-methylfuran and one or more epoxides are added to the methylene chloride. The total amount of stabilizers will preferably be between 0.05 and 10%, and in particular between 0.1 and 5% by weight of the methylene chloride to be treated. Larger doses of stabilizers may also be used, but are of little interest from the point of view of economy. Smaller doses may also be used, but are usually less effective.

Examples of epoxides which may be used are those which contain from 2 to 8 carbon atoms and which may or may not be substituted by halogens or hydroxyl groups, more particularly ethylene oxide, epoxy propane, the epoxy butanes, epichlorohydrin, isobutylene oxide, glycidol, cyclohexene oxide, and styrene oxide.

Particularly suitable mixtures of stabilizers will contain 2-methylfuran and epoxybutane or glycidol.

To the mixtures of stabilizers according to the invention there may advantageously be added one or more acetylene alcohols, such as for example propargyl alcohol, 2-methyl-3-butyn-2-ol, 3-methyl-1-pentyn-3-ol, 3-methyl-1-nonyn-3-ol, butyn-1,4-diol, 2,5-dimethyl-3-hexyne-2,5-diol, 2,5-diphenyl-3-hexyne-2,5-diol, 3,6-dimethyl-4-octyne-3,6-diol, 4,7-dimethyl-5-decyne-4,7-diol, or 2,4,7,9-tetramethyl-5-decyne-4,7-diol.

The amount of acetylene alcohols will generally be between 0.02 and 5%, preferably between 0.05 and 2%, by weight of the methylene chloride to be treated. Larger doses of acetylene alcohols may also be used, but they are of little interest from the point of view of economy.

It is obvious that the process of stabilization of methylene chloride by the mixture of stabilizers according to the invention may be combined with the use of one or more other stabilizers which are already known.

The invention may also be applied to the stabilization of mixtures containing methylene chloride, and particularly to the stabilization of aerosol compositions containing methylene chloride.

The following examples, which are not of a limitative nature, show the remarkable results obtained by one embodiment of the invention.

EXAMPLE 1

In order to evaluate the influence of methylene chloride on the corrosion of aerosol cans in the presence of water, the corrosivity of a mixture comprising propellant (dichlorodifluoromethane) + solvent (ethanol) + water + unstabilized methylene chloride was compared with that of the same mixture containing no methylene chloride.

The stabilization action of mixtures comprising 1,2-epoxybutane + 2-methylfuran and of glycidol + 2-methylfuran on methylene chloride in a mixture of this kind was then examined.

The test consisted in introducing into aerosol cans of tinned iron (CROWN CORK brand) a composition containing 40% by weight dichlorodifluoromethane, 40% by weight stabilized or unstabilized methylene chloride, and 20% by weight technical ethanol containing 6% by volume of water. The cans are filled to 75% of their capacity; they are disposed vertically and kept at 40° C. Corrosion is observed after two months.

A compartive test is made with a composition containing only dichlorodifluoromethane and ethanol with 6% of volume of water, in the same proportions as indicated above.

Table I below shows the corrosion observed after two months when using the different stabilizing compositions. The numeral 1 indicates that the casing has an appearance identical to that of the new casing (no corrosion); 2 indicates that there is slight general corrosion; 3 that there is heavy general corrosion; 4 that there are some pits, and 5 that there are numerous pits. The formulae bearing the letter R are given by way of comparison.

Table I

| Formula No. | Composition | | Extent of corrosion Cylinder | Seam | Valve |
|---|---|---|---|---|---|
| O | Composition containing no $CH_2Cl_2$ | | 1 | 4 | 1 |
| 1 R | | unstabilized | 2 + 5 | 3 + 5 | 1 |
| 2 R | Compositions | + 5 g/l 1,2-epoxybutane | 4 | 2 + 5 | 1 |
| 3 R | containing | + 5 g/l 2-methylfuran* | 3 + 5 | 3 + 5 | 1 |
| 4 R | $CH_2Cl_2$ | + 1 g/l 2-methylfuran* | 2 + 4 | 3 + 5 | 1 |
| 5 | | + 2 g/l 1,2-epoxybutane + 2 g/l 2-methylfuran* | 1 | 4 | 1 |
| 6 | | + 2 g/l glycidol + 2 g/l 2-methylfuran* | 1 | 4 | 1 |

*Stabilized by N-methylpyrrole

In all cases the corrosion observed is on the metal in contact with the liquid phase. No corrosion in the vapour phase was observed in any instance.

Examination of Table I shows that, in the presence of water, methylene chloride which is either not stabilized or is stabilized by epoxybutane or 2-methylfuran alone gives rise to not inconsiderable corrosion of the cans. On the other hand, it is seen that when a mixture of 2-methylfuran + epoxybutane or glycidol is used, the corrosion due to the presence of methylene chloride is suppressed.

EXAMPLE 2

The same test as that described in Example 1 was made in aerosol cans of monobloc aluminium (SNIA VISCOSA brand).

Anhydrous ethanol and technical ethanol containing 6% by volume of water were used alternately.

The results of the tests are given in Table II.

In this case, as in the case of Example 1, the corrosion observed was on the metal in contact with the liquid phase; in no case was corrosion in the vapour phase observed.

Table II

| Formula No. | Composition | | Anhydrous ethanol ($H_2O<0.5\%$ by volume) | | Technical ethanol (6% by volume $H_2O$) | |
|---|---|---|---|---|---|---|
| | | | Extent of corrosion | | | |
| | | | Cylinder | Valve | Cylinder | Valve |
| 0 | Composition containing no $CH_2Cl_2$ | | 4 | 1 | 4 | 1 |
| 1 R | | unstabilized | 4 | 1 | 5 | 1 |
| 2 R | | + 5 g/l 1,2-epoxybutane | 1 | 1 | 5 | 1 |
| 3 R | Compositions | + 5 g/l 2-methylfuran* | 4 | 1 | 5 | 1 |
| 4 R | containing | + 1 g/l 2-methylfuran* | 4 | 1 | 5 | 1 |
| 5 | $CH_2Cl_2$ | + 2 g/l 1,2-epoxybutane* | | | | |
| | | + 2 g/l 2-methylfuran* | 1 | 1 | 4 | 1 |
| 6 | | + 2 g/l glycidol | | | | |
| | | + 2 g/l 2-methylfuran* | | | 1 | 1 |

*Stabilized by N-methylpyrrole

The tests summarised in Table II show that in the absence of water the reference composition has a certain corrosivity in relation to aluminium. This corrosivity is not increased by the addition of methylene chloride in the unstabilized form or stabilized by 2-methylfuran. On the other hand, this corrosion is eliminated with methylene chloride stabilized by means of epoxybutane alone or mixed with 2-methylfuran.

In the presence of water the reference composition likewise exhibits corrosivity in relation to aluminium. This corrosivity is increased by the addition of methylene chloride either unstabilized or stabilized by 2-methylfuran or epoxybutane. The use of the mixture epoxybutane + 2-methylfuran makes it possible to eliminate corrosion due to the presence of methylene chloride, while the utilisation of the mixture glycidol + 2-methylfuran enables all corrosion to be eliminated.

EXAMPLE 3

Supplementary tests have shown that the addition of butyn-1,4-diol at the rate of 2 grams per liter of methylene chloride further improves resistance to corrosion and reduces the final content of chloride ions after storage for 3 months.

We claim:

1. A methylene chloride composition containing stabilizing quantities of 2-methylfuran and one or more epoxides.

2. The composition according to claim 1 wherein the total amount of stabilizers is between 0.05 and 10% by weight of the methylene chloride.

3. The composition according to claim 2 wherein the total amount of stabilizers is between 0.1 and 5% by weight of the methylene chloride.

4. The composition according to claim 1 wherein the epoxide is epoxy butane.

5. The composition according to claim 1 wherein the epoxide is glycidol.

6. The composition according to claim 1 and further containing an acetylene alcohol.

7. The composition according to claim 6 wherein the acetylene alcohol is butyn-1,4-diol.

8. The composition according to claim 1 wherein the epoxides are those containing 2 to 8 carbon atoms substituted or not by halogens or hydroxyl groups.

9. The composition according to claim 1 wherein the total amount of stabilizers is between 0.05 and 10% by weight of the methylene chloride and wherein the epoxides are those containing 2 to 8 carbon atoms substituted or not by halogens or hydroxyl groups.

* * * * *